United States Patent
Kang et al.

(10) Patent No.: US 10,416,437 B2
(45) Date of Patent: Sep. 17, 2019

(54) ENDOSCOPY SYSTEM

(71) Applicant: INTHESMART Co., Ltd., Seoul (KR)

(72) Inventors: Uk Kang, Seoul (KR); Ilhyung Shin, Jeju (KR)

(73) Assignee: INTHESMART INC., Seoul (KR)

( * ) Notice: Subject to any disclaimer, the term of this patent is extended or adjusted under 35 U.S.C. 154(b) by 0 days.

(21) Appl. No.: 16/185,363

(22) Filed: Nov. 9, 2018

(65) Prior Publication Data

US 2019/0094518 A1    Mar. 28, 2019

Related U.S. Application Data

(63) Continuation of application No. 15/335,463, filed on Oct. 27, 2016, now Pat. No. 10,162,169.

(30) Foreign Application Priority Data

Jun. 24, 2016 (KR) .................. 10-2016-0079109

(51) Int. Cl.
*G02B 23/24* (2006.01)
*A61B 1/00* (2006.01)
(Continued)

(52) U.S. Cl.
CPC ...... *G02B 23/2469* (2013.01); *A61B 1/00006* (2013.01); *A61B 1/00009* (2013.01); *A61B 1/00025* (2013.01); *A61B 1/00045* (2013.01); *A61B 1/04* (2013.01); *A61B 1/05* (2013.01); *A61B 1/0669* (2013.01); *A61B 1/07* (2013.01);
(Continued)

(58) Field of Classification Search
CPC ... A61B 1/00009; A61B 1/0005; A61B 1/045; A61B 1/0638
See application file for complete search history.

(56) References Cited

U.S. PATENT DOCUMENTS 6,361,490 B1 * 3/2002 Irion .................. A61B 5/0059
                                                          434/267
10,162,169 B2 * 12/2018 Kang ................ A61B 1/00006
(Continued)

FOREIGN PATENT DOCUMENTS

JP    2005-328883 A    12/2005
JP    2006-310613 A    11/2006
(Continued)

*Primary Examiner* — Ali Alavi
(74) *Attorney, Agent, or Firm* — Patent Office of Dr. Chung Park

(57) ABSTRACT

An endoscope system includes: a first light source unit having a first terminal to which power is supplied; a second light source having a second terminal to which power is supplied; a light guide unit for guiding light of the first and second light source units to the inside of a target object; an image sensing unit configured to sense the light reflected from the target object; and an image signal processing unit configured to process signal from the sensing unit and display on a display unit. The first light source unit includes first and second perimeter units, the second light source unit includes a third perimeter unit, and a fourth perimeter unit, and the first and second terminals are provided in the second perimeter unit or the fourth perimeter unit other than an area between the first perimeter unit and the third perimeter unit that face each other.

5 Claims, 9 Drawing Sheets

(51) Int. Cl.
*A61B 1/04* (2006.01)
*A61B 1/06* (2006.01)
*A61B 1/07* (2006.01)
*H04N 5/225* (2006.01)
*A61B 1/05* (2006.01)

(52) U.S. Cl.
CPC ....... *G02B 23/2484* (2013.01); *H04N 5/2256* (2013.01); *H04N 2005/2255* (2013.01)

(56) References Cited

U.S. PATENT DOCUMENTS

2017/0332880 A1* 11/2017 Ito .......................... G01N 21/27
2018/0249889 A1*  9/2018 Imai ................... A61B 1/00009

FOREIGN PATENT DOCUMENTS

| | | |
|---|---|---|
| JP | 2007-148418 A | 6/2007 |
| KR | 10-2007-0071556 A | 7/2007 |
| KR | 10-2014-0008128 A | 1/2014 |

* cited by examiner

[Fig. 1]
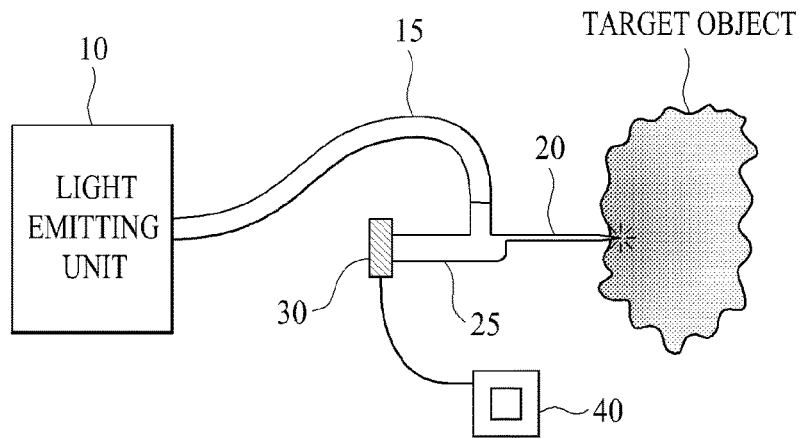
[Fig. 2]
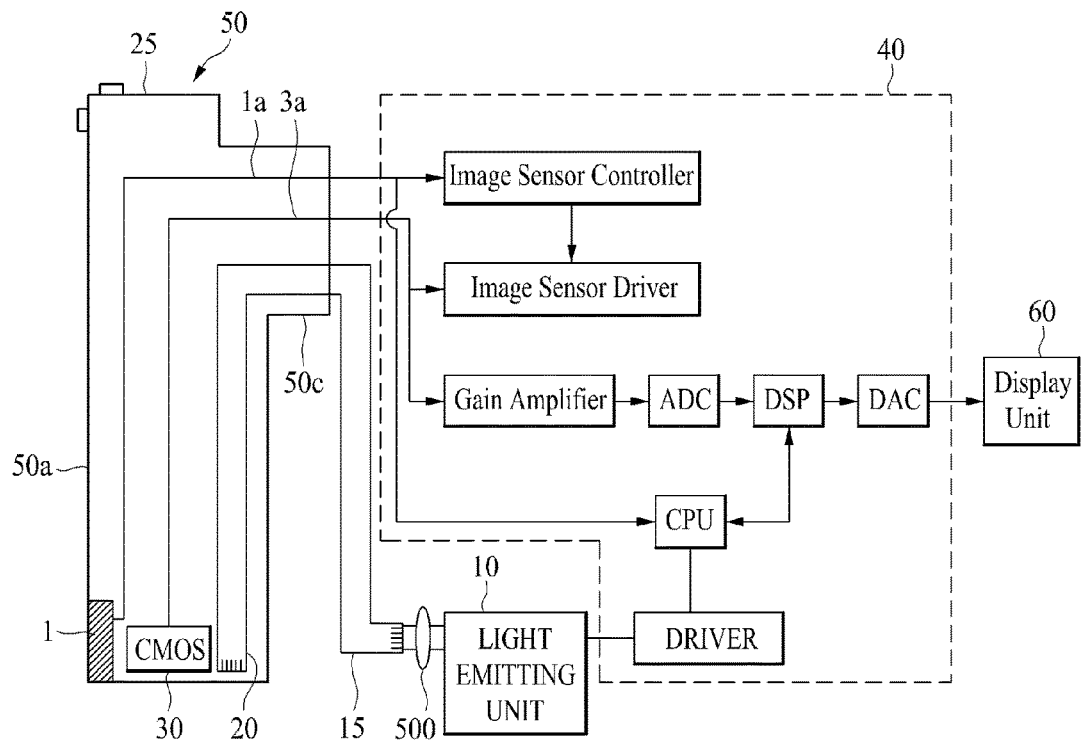

[Fig. 3]
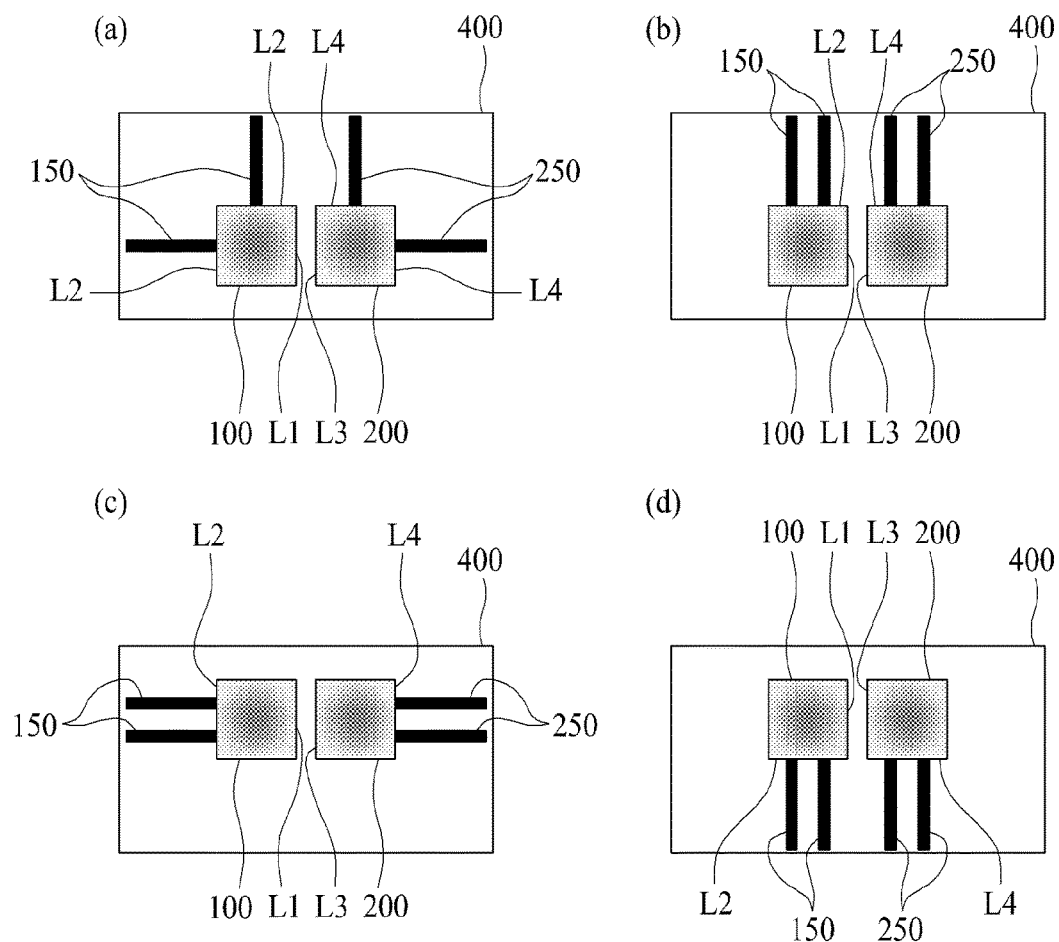

[Fig. 4]
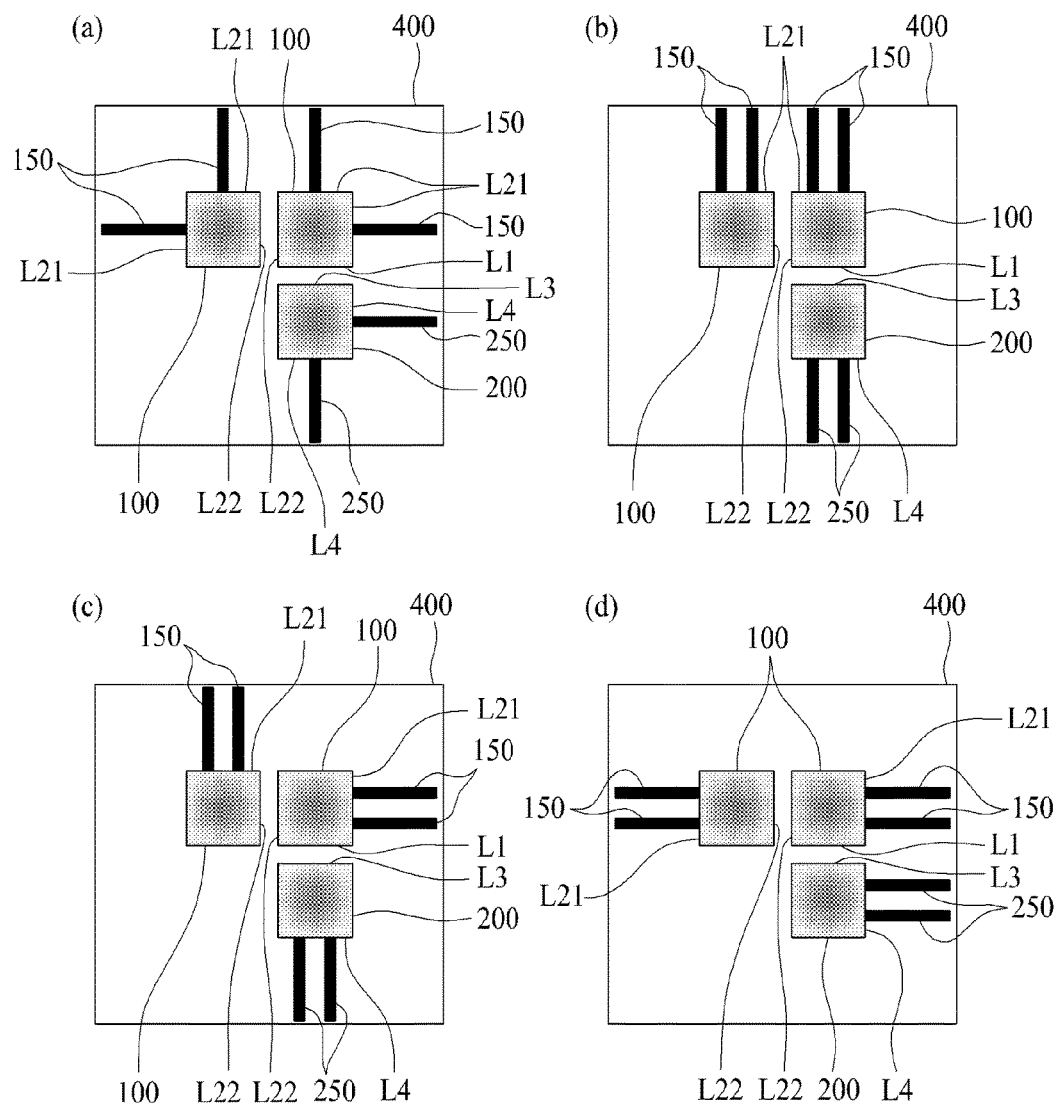

[Fig. 5]
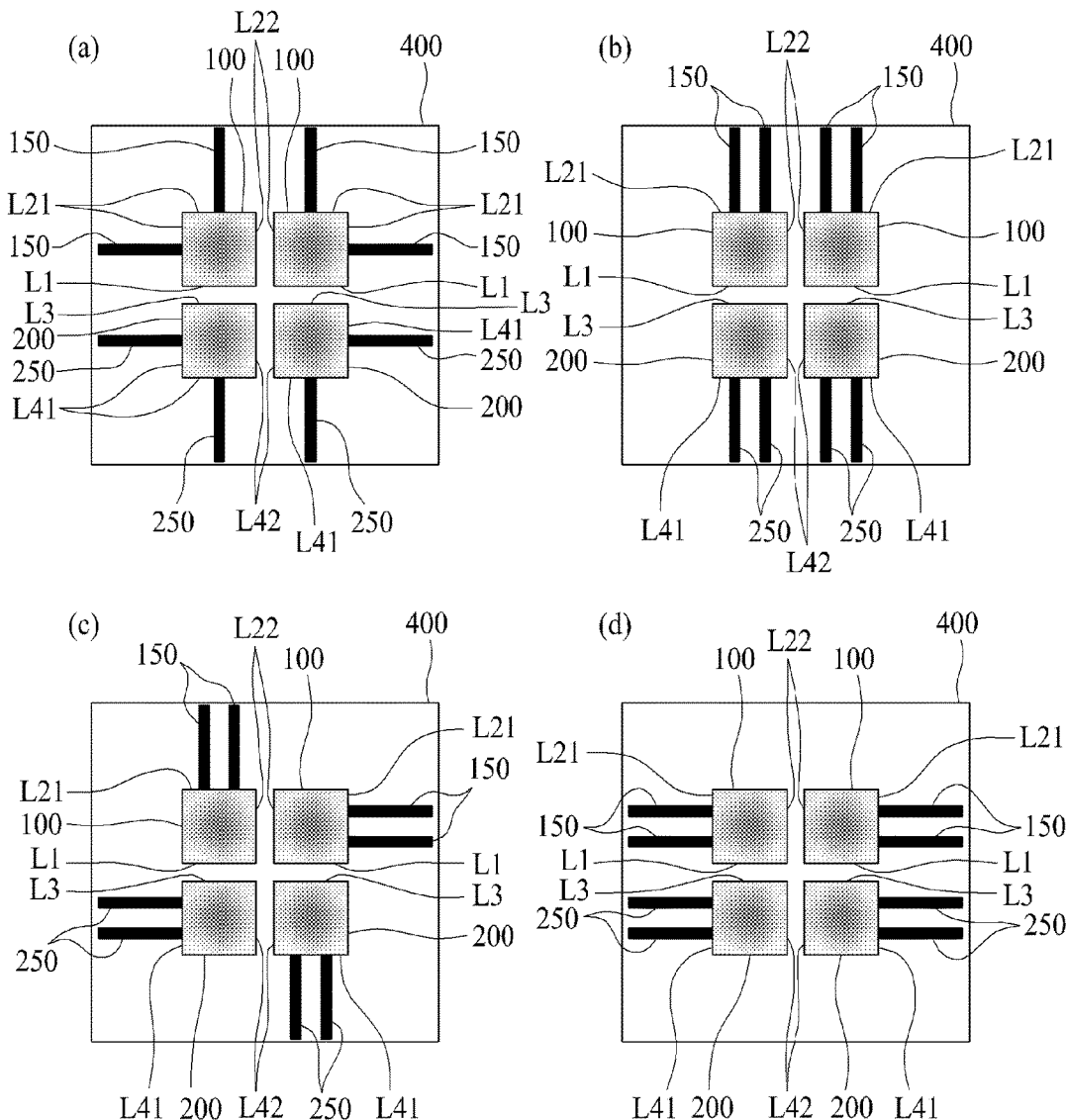

[Fig. 6]
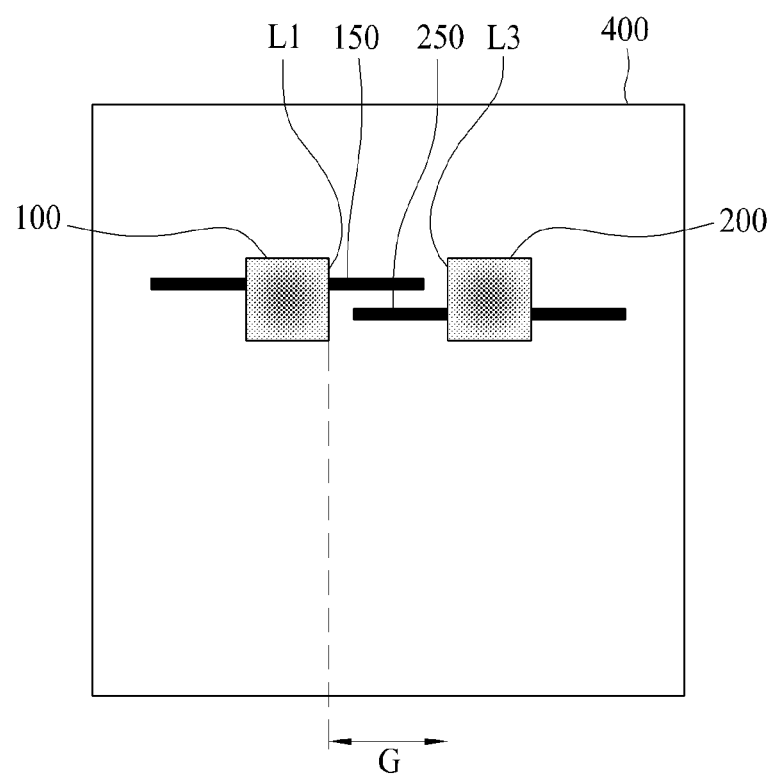

[Fig. 7]
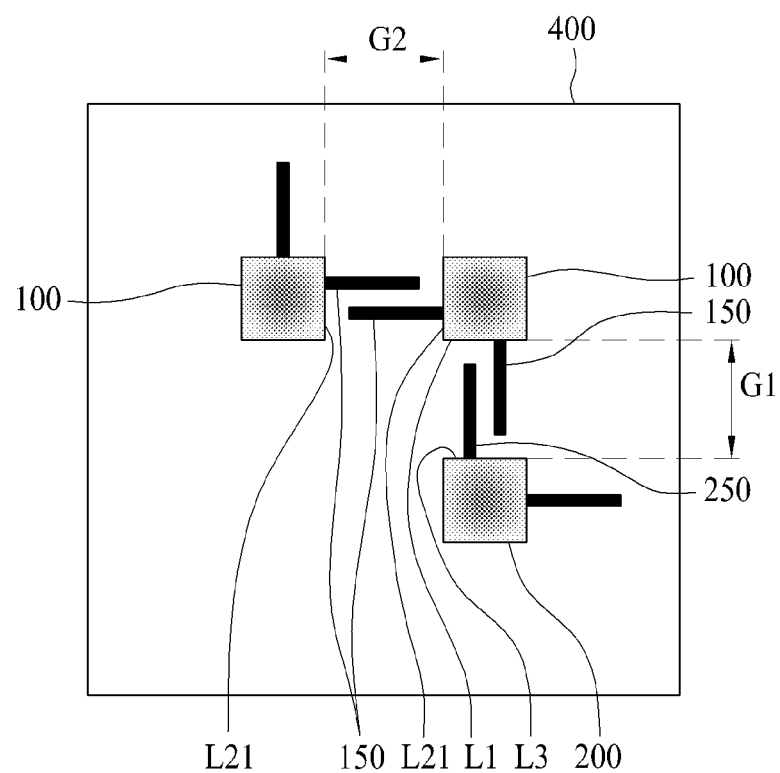

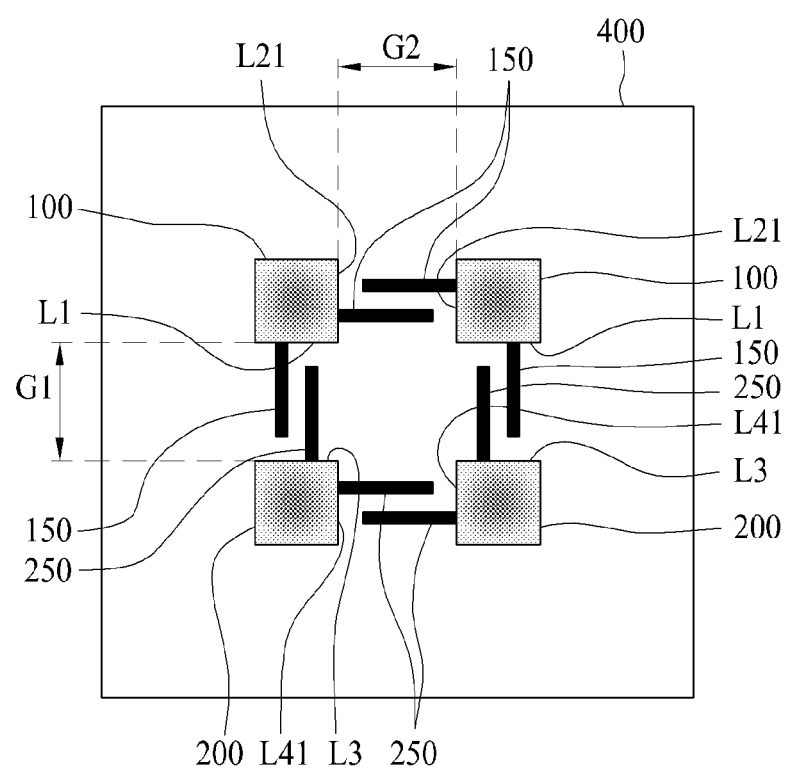
[Fig. 8]

[Fig. 9]
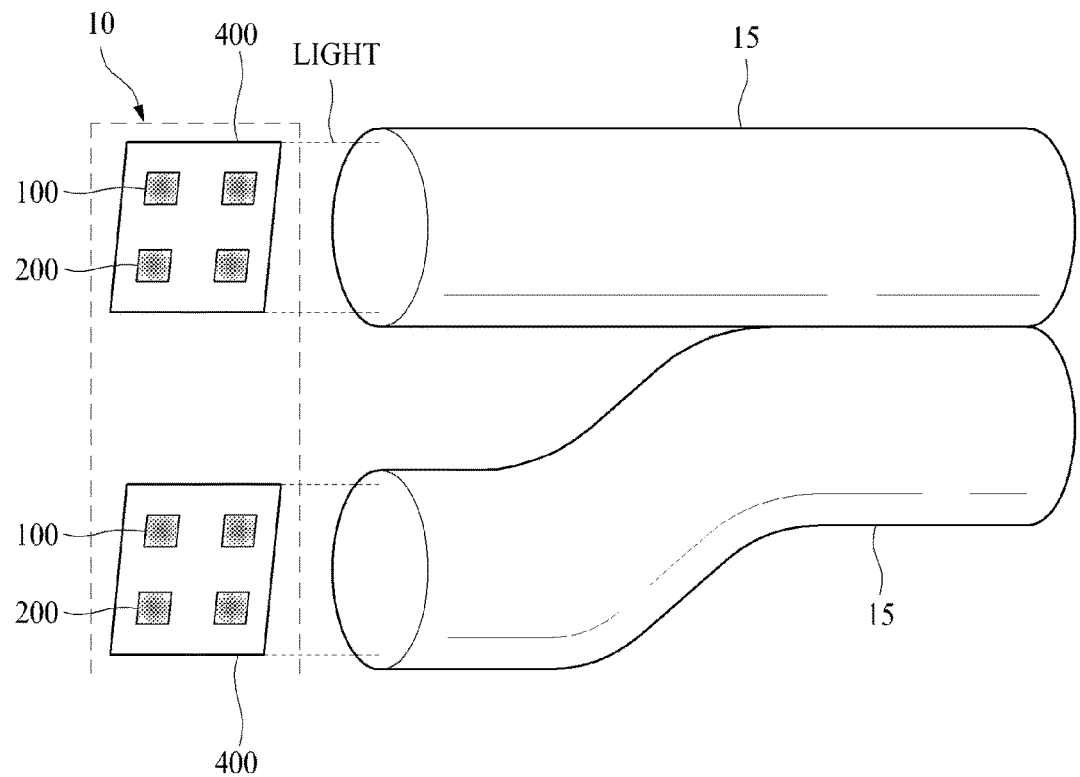
[Fig. 10]
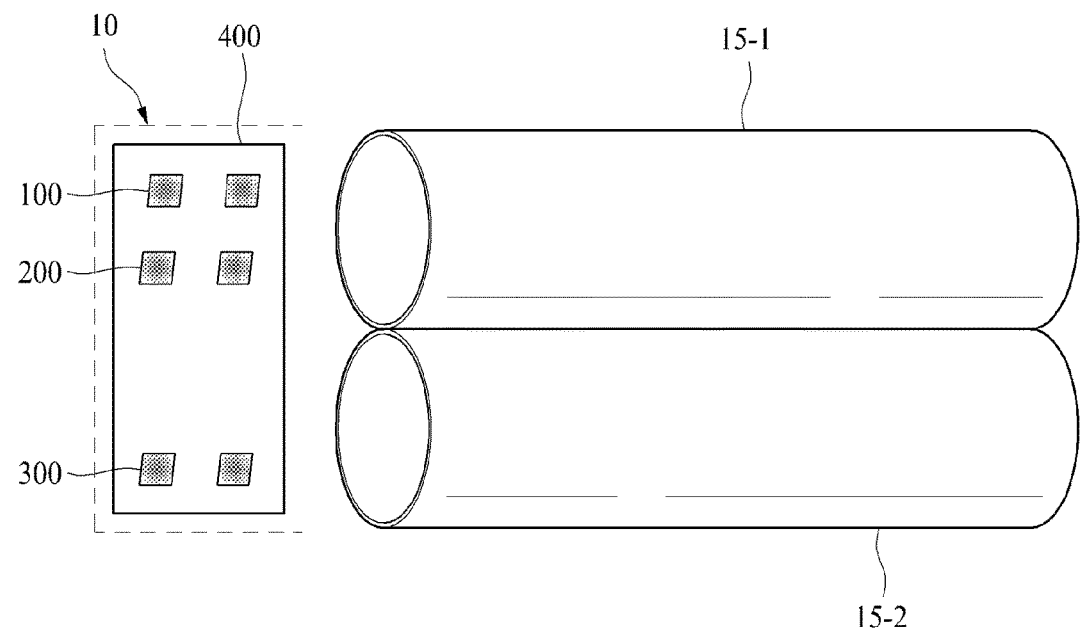

[Fig. 11]
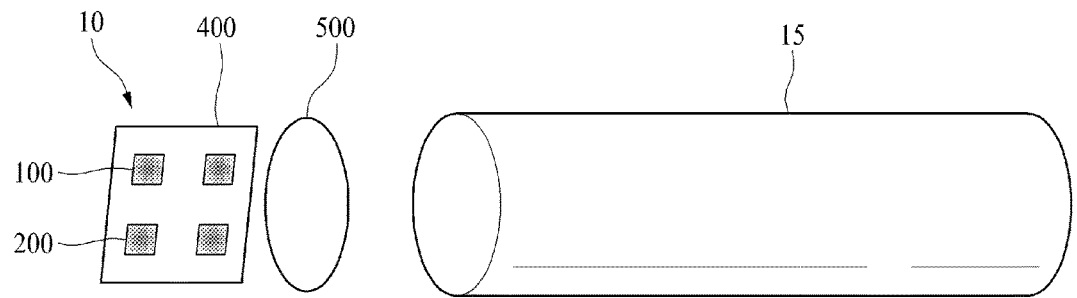
[Fig. 12]
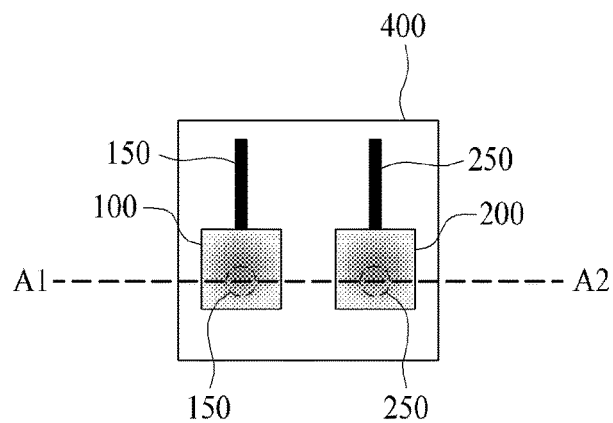
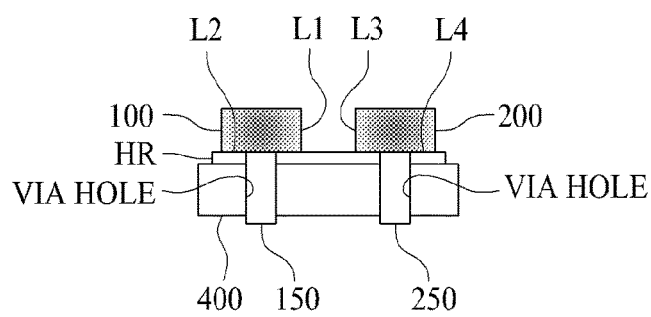

ENDOSCOPY SYSTEM

CROSS-REFERENCE TO RELATED APPLICATIONS

This application is a continuation of U.S. patent application Ser. No. 15/335,463 filed Oct. 27, 2016, which claims priority under 35 U.S.C. § 119 the priority benefit of Korean Patent Application No. 10-2016-0079109 filed on Jun. 24, 2016, the subject matter of which is incorporated herein by reference.

BACKGROUND OF THE INVENTION

Field of the Invention

The present disclosure relates to an endoscopy system.

Description of the Related Art

An endoscope system requires a high degree of stability as it is used for medical internal check. The endoscopic system emits a light to the inside of a target object and senses a reflected light to generate a corresponding image of the inside of the target object.

At this time, since a doctor or an operator manipulates the endoscope system, as the size of the endoscope system becomes compact, the operation of the endoscope system may be facilitated.

Accordingly, various studies to reduce the size of the endoscope system are in progress.

SUMMARY OF THE INVENTION

The present disclosure has been made in view of the above problems, and provides an endoscope system with a structure that can reduce a size.

In accordance with an aspect of the present disclosure, an endoscope system includes: a first light source unit configured to be provided on a substrate, and to have a first terminal to which power is supplied; a second light source configured to be provided on the substrate, and to have a second terminal to which power is supplied; a light guide unit configured to guide a light of the first light source unit and the second light source unit to the inside of a target object; an image sensing unit configured to sense the light reflected and reached from the target object to convert into an image signal; and an image signal processing unit configured to process the image signal to display on a display unit, wherein the first light source unit comprises a first perimeter unit, and a second perimeter unit other than the first perimeter unit, the second light source unit comprises a third perimeter unit, and a fourth perimeter unit other than the third perimeter unit, and the first terminal and the second terminal are provided in the second perimeter unit or the fourth perimeter unit other than an area between the first perimeter unit and the third perimeter unit that face each other.

In a case of including a plurality of the first light source units, the first terminal is provided in an area other than an area where the plurality of the first light source units face each other among an area of the second perimeter unit.

In a case of including a plurality of the second light source units, the second terminal is provided in an area other than an area where the plurality of the second light source units face each other among an area of the fourth perimeter unit.

The endoscope system further includes an optical unit configured to input a light of the first light source unit and the second light source unit into an optical fiber.

The second perimeter unit is a side surface or a rear side surface of the first light source unit.

When the second perimeter unit is the rear side surface of the first light source unit, a via hole through which the first terminal passes is formed in an area of the substrate which is overlapped with the rear side surface of the first light source unit.

The fourth perimeter unit is a side surface or a rear side surface of the second light source unit.

When the fourth perimeter unit is the rear side surface of the second light source unit, a via hole through which the second terminal passes is formed in an area of the substrate which is overlapped with the rear side surface of the second light source unit.

The endoscope system further includes a plurality of the substrates, and a single optical fiber is provided for each substrate so that the light of the first light source unit and the second light source unit of the substrate is input to the optical fiber.

The endoscope system further includes: a third light source unit configured to be provided on the substrate; a first optical fiber to which the light of the first light source unit and the second light source unit is input; and a second optical fiber to which the light of the third light source unit is input.

The second light source unit does not emit light when the first light source unit emits light, and the second light source unit emits light when the first light source unit does not emit light.

BRIEF DESCRIPTION OF THE DRAWINGS

The objects, features and advantages of the present disclosure will be more apparent from the following detailed description in conjunction with the accompanying drawings, in which:

FIG. 1 illustrates an implementation of an endoscope system according to an embodiment of the present disclosure;

FIG. 2 is a block diagram illustrating an endoscope system according to an embodiment of the present disclosure;

FIG. 3 to FIG. 5 illustrate a light emitting unit of an endoscope system according to an embodiment of the present disclosure;

FIG. 6 to FIG. 8 illustrate a comparative example of a light emitting unit of an endoscope system according to an embodiment of the present disclosure;

FIG. 9 and FIG. 10 illustrate a relationship between the light emitting unit and an optical fiber;

FIG. 11 illustrates a relationship between the light emitting unit, an optical unit, and the optical fiber; and FIG. 12 illustrates an example of a cross section of the light emitting unit.

DETAILED DESCRIPTION OF EXEMPLARY EMBODIMENTS

Exemplary embodiments of the present disclosure are described with reference to the accompanying drawings in detail. The same reference numbers are used throughout the drawings to refer to the same or like parts. Detailed descriptions of well-known functions and structures incorporated herein may be omitted to avoid obscuring the subject matter of the present disclosure.

The terms and words used in the following description and claims are not limited to the bibliographical meanings, but, are merely used by the inventor to enable a clear and consistent understanding of the present disclosure. It is to be understood that the singular forms "a," "an," and "the" include plural referents unless the context clearly dictates otherwise.

In the present disclosure, the terms such as "include" and/or "have" may be construed to denote a certain characteristic, number, step, operation, constituent element, component or a combination thereof, but may not be construed to exclude the existence of or a possibility of addition of one or more other characteristics, numbers, steps, operations, constituent elements, components or combinations thereof.

FIG. 1 illustrates an implementation of an endoscope system according to an embodiment of the present disclosure.

Referring to FIG. 1, the endoscope system according to an embodiment of the present disclosure may include a light emitting unit 10, an optical fiber 15, a light guide unit 20, an image sensing unit 30, and an image signal processing unit 40.

The light emitting unit 10 may emit light of various wavelengths such as visible light, ultraviolet rays, and infrared rays. The configuration of the light emitting unit 10 is described in more detail later.

The optical fiber 15 may provide a path for the light of the light emitting unit 10 toward the light guide unit 20.

To this end, the optical fiber 15 may be connected to a handle 25, and the handle 25 may be coupled to the light guide unit 20. A doctor or an operator may manipulate the endoscope system according to an embodiment of the present disclosure through the handle 25.

The light guide unit 20 may induce the light generated by the light emitting unit 10 to the inside of a target object. The target object may be a person, an animal, a product, or the like, but it is not limited thereto.

The image sensing unit 30 may sense the light which is reflected from the target object and convert the sensed light into an image signal. To this end, the image sensing unit 30 may include a charge-coupled device (CCD) or a complementary metal oxide semiconductor (CMOS), but it is not limited thereto.

The image signal processing unit 40 may process the image signal to display on a display unit (not shown) such as a monitor or TV.

The endoscopic system according to an embodiment of the present disclosure is not limited to a structure of FIG. 1.

FIG. 2 is a block diagram illustrating an endoscope system according to an embodiment of the present disclosure.

As shown in FIG. 2, the endoscope system according to an embodiment of the present disclosure may include an endoscope 50 which can observe the light of a specific wavelength, an image signal processing unit which drives the endoscope 50 and which processes a signal of an image picked up by the endoscope 50, and a display unit 60 which displays the pick-up image of a target object.

The endoscope 50 may include a flexible or a rigid insertion unit 50a that is inserted into the target object at which light scarcely arrives, a handle 25 provided to the insertion unit 50a, and a universal cord unit 50c extended from the side of the handle 25, and may be electrically connected to the image signal processing unit 40 through the universal cord unit 50c.

In addition, a main body of the endoscope 50 may be mainly configured of the insertion unit 50a and the handle 25, and the pickup image signal and control signals may be transmitted to the image signal processing unit 40 via a cable 1a, 3a.

The image sensing unit 30 such as CMOS or CCD, a motion detection sensor 1 such as a gyro sensor or an acceleration sensor, and a forceps hole may be provided to an end of the insertion unit 50a. Since the forceps hole is already well known, a description thereof is omitted.

The image sensing unit 30 may be connected to an image sensor driver through a bundled cable 3a having a plurality of signal wires 3a, and the motion detection sensor 1 may also be connected via a cable 1a.

The light guide unit 20 may be connected to the image signal processing unit 40 through the universal cord unit 50c in the insertion unit 50a. The light guide unit 20 may guide the light emitted from the light emitting unit 10 to be outputted to the end of the insertion unit 50a.

The image signal processing unit 40 is described only for components related to the image pickup, and a description of other general components needed for driving is omitted.

The image signal processing unit 40 may, at least, include an image sensor driver, a gain amplifier, an analog-to-digital converter (ADC), a digital signal processor (DSP), a digital-to-analog converter (DAC), and a controller (CPU).

The gain amplifier may amplify the image signal according to an appropriate gain. The analog-to-digital converter (ADC) may convert the amplified image signal into a digital signal. The digital signal processor (DSP) may perform the image processing for the image signal of a digital signal type. The digital-to-analog converter (DAC) may convert the image processed image signal into an analog signal.

The controller (CPU) may control the overall operation of the endoscope system according to an embodiment of the present disclosure, and may control the image processing procedure.

The light emitting unit 10 may be driven by receiving power by a driver, and the driver may be controlled by the controller (CPU).

In FIG. 2, an optical unit 500 may be provided between the light emitting unit 10 and the optical fiber 15, but a light of the light emitting unit 10 may be inputted to the optical fiber 15 without having the optical unit 500.

The structure of FIG. 2 is just an example of the endoscope system according to an embodiment of the present disclosure, but it is not limited thereto.

In the following drawings, the light emitting unit 10 is mainly shown for the convenience of explanation. As shown in FIG. 3 to FIG. 5, the light emitting unit 10 may include a first light source unit 100, a second light source unit 200, and a substrate 400. In addition, the light emitting unit 10 may further include a third light source unit 300, and the third light source unit 300 is described in detail later.

The endoscopic system according to an embodiment of the present disclosure may include the substrate 400, the first light source unit 100, the second light source unit 200, the light guide unit 20, the image sensing unit 30, and the image signal processing unit 40.

The first light source unit 100 may be provided in the substrate 400, and may have a first terminal 150 to which power is supplied.

The second light source unit 200 may be provided in the substrate 400, and may have a second terminal 250 to which power is supplied.

At this time, the first light source unit 100 and the second light source unit 200 may include LED, but not limited thereto and may have a light source other than LED.

The light guide unit 20 may guide the light of the first light source unit 100 and the second light source unit 200 to the inside of a target object.

The image sensing unit 30 may sense the light that is reflected and reached from the target object and convert the sensed light into an image signal.

The image signal processing unit 40 may process the image signal to display on a display unit.

Since the light guide unit 20, the image sensing unit 30, and the image signal processing unit 40 are described above in detail, a description thereof is omitted.

The first light source unit 100 may include a first perimeter portion (L1), and a second perimeter portion (L2, L21, L22) other than the first perimeter portion (L1). The second light source unit 200 may include a third perimeter portion (L3), and a fourth perimeter portion (L4, L41, L42) other than the third perimeter portion (L3).

For example, as shown in FIGS. 3 to 5, the second perimeter portion (L2, L21, L22) may be extended from the first perimeter portion (L1), or may be located opposite to the first perimeter portion (L1). The fourth perimeter portion (L4, L41, L42) may also be extended from the third perimeter portion (L3) or may be located opposite to the third perimeter portion (L3).

The first terminal 150 and the second terminal 250 may be provided in the second perimeter portion (L2, L21) or the fourth perimeter portion (L4, L41, L42) other than an area between the first perimeter portion (L1) and the third perimeter portion (L3) that face each other.

Due to such a structure, a gap between the first light source unit 100 and the second light source unit 200 may be reduced, such that the size of the substrate 400 and the light emitting unit 10 can be reduced. That is, as shown in FIG. 6, differently from the embodiment of the present disclosure, when the first terminal 150 and the second terminal 250 exist between the first perimeter portion (L1) of the first light source unit 100 and the third perimeter portion (L3) of the second light source unit 200, the gap (G) between the first light source unit 100 and the second light source unit 200 may become larger, such that the size of the substrate 400 and the light emitting unit 10 may become larger.

In the case of FIG. 3, a single first light source unit 100 and a single second light source unit 200 may be provided in the substrate 400. In the case of FIG. 4, two first light source units 100 and a single second light source unit 200 may be provided in the substrate 400. In the case of FIG. 5, two first light source units 100 and two second light source units 200 may be provided in the substrate 400.

At this time, the first terminal 150 and the second terminal 250 may be provided in the second perimeter portion (L2, L21) and the fourth perimeter portion (L4, L41) other than an area between the first perimeter portion (L1) and the third perimeter portion (L3) that face each other.

Differently from FIG. 4 and FIG. 5, the number of the first light source unit 100 and the second light source unit 200 may be changed.

Meanwhile, as shown in FIG. 4 and FIG. 5, the endoscope system according to an embodiment of the present disclosure may include a plurality of first light source units 100. In this case, the first terminal 150 may be provided in an area (L21) other than an area (L22) where the plurality of first light source units 100 face each other among an area (L2, L21) of the second perimeter portion of the plurality of first light source units 100.

For example, as shown in FIG. 4(a), in the upper side, two first light source units 100 may be disposed on the substrate 400. In this case, the first light source unit 100 in the right side faces the second light source unit 200.

As explained above, the first terminal 150 and the second terminal 250 are not provided between the first perimeter portion (L1) of the first light source unit 100 and the third perimeter portion (L3) of the second light source unit 200. In addition, the first terminal 150 is not provided in the area (L22) of the first light source units 100 facing each other among the area (L2, L21) of the second perimeter portion of the plurality of first light source units 100. The first terminal 150 may be provided in the area (L21) other than the above mentioned area (L22).

Accordingly, the size of the substrate 400 and the light emitting unit 10 may be decreased. That is, as shown in FIG. 7, differently from the embodiment of the present disclosure, when the first terminal 150 and the second terminal 250 exist between the first perimeter portion (L1) of the first light source unit 100 and the third perimeter portion (L3) of the second light source unit 200, the gap (G1) between the first light source unit 100 and the second light source unit 200 may become larger, such that the size of the substrate 400 and the light emitting unit 10 may become larger.

Further, since the first terminal is disposed between the second perimeter portions (L21) of the first light source units 100 facing each other, the gap (G2) between the first light source units 100 may become larger. Accordingly, the size of the substrate 400 and the light emitting unit 10 may become larger.

Meanwhile, as shown in FIG. 5, the endoscope system according to an embodiment of the present disclosure may include a plurality of second light source units 200. In this case, the second terminal 250 may be provided in an area (L41) other than an area (L42) where the plurality of second light source units 200 facing each other among the area of the fourth perimeter portion (L4, L41, L42).

For example, as shown in FIG. 5(a), two first light source units 100 may be disposed in the upper side, and two second light source units 200 may be disposed in the lower side. The first terminal 150 and second terminal 250 are not disposed between the first perimeter portion (L1) of the first light source unit 100 and the third perimeter portion (L3) of the second light source unit 200.

In addition, the first terminal 150 may not be disposed between the facing second perimeter portions (L22) of the first light source units 100, and the first terminal 150 may be provided in the remaining second perimeter portions (L21).

Similarly, the second terminal 250 may not be disposed between the facing fourth perimeter portions (L42) of the second light source units 200, and the second terminal 250 may be provided in the remaining fourth perimeter portions (L42).

Accordingly, the size of the substrate 400 and the light emitting unit 10 may become smaller.

Dissimilarly to this, as shown in FIG. 8, when the first terminal 150 and the second terminal 250 are disposed between the facing first light source unit 100 and the second light source unit 200, the gap (G1) between the first light source unit 100 and the second light source unit 200 may increase. In addition, when the first terminal 150 is disposed between the plurality of first light source units 100 and the second terminal 250 is disposed between the plurality of the second light source units 200, the gap (G2) may increase.

Meanwhile, as shown in FIG. 9, when the endoscope system according to an embodiment of the present disclosure includes a plurality of substrates 400, the optical fiber 15 may be provided for each substrate 400 such that the light of the first light source unit 100 and the second light source unit 200 of the substrate 400 may be inputted to the optical fiber 15.

In addition, as shown in FIG. 10, the endoscope system according to an embodiment of the present disclosure may further include a third light source unit 300 provided in the substrate 400, a first optical fiber 15-1 to which the light of the first light source unit 100 and the second light source unit 200 is inputted, and a second optical fiber 15-2 to which the light of the third light source unit 300 is inputted.

Since the diameter of the optical fiber 15 is small, as the light emitting unit 10 or the substrate 400 becomes small, the possibility that the light is inputted to the optical fiber 15 may increase. As described above, in the case of the endoscope system according to an embodiment of the present disclosure, as the size of the substrate 400 or the light emitting unit 10 is small, it is possible to increase the amount of light which is inputted to the optical fiber 15.

As shown in FIG. 9 and FIG. 10, since the size of the substrate 400 and the light emitting unit 10 is small, most of the light may be inputted to the optical fiber 15 by reducing the distance between the light emitting unit 10 and the optical fiber 15 even if there is no optical unit 500 such as collimator.

Dissimilarly to this, as shown in FIG. 8, the endoscope system according to an embodiment of the present disclosure may further include the optical unit 500 which inputs the light of the first light source unit 100 and the second light source unit 200 into the optical fiber 15.

In this case, the optical unit 500 may include a collimator, and may enhance a light efficiency by inputting a parallel light which is made by the light emitted by optical unit 500 to the optical fiber 15.

Meanwhile, as shown in FIG. 3 to FIG. 5, the second perimeter portion (L2, L21, L22) may be the side surface of the first light source unit 100, or, as shown in FIG. 12, may be the rear side surface of the first light source unit 100. Thus, when the second perimeter portion (L2, L21, L22) is the rear side surface of the first light source unit 100, a via hole through which the first terminal 150 passes may be formed in the substrate 400 area which is overlapped with the rear side surface of the first light source unit 100.

In addition, as shown in FIG. 3 to FIG. 5, the fourth perimeter portion (L4, L41, L42) may be the side surface of the second light source unit 200, or, as shown in FIG. 12, may be the rear side surface of the second light source unit 200. Thus, when the fourth perimeter portion (L4, L41, L42) is the rear side surface of the second light source unit 200, a via hole through which the second terminal 250 passes may be formed in the substrate 400 area which is overlapped with the rear side surface of the second light source unit 200.

The cross-section according to A1-A2 is shown in the lower side of FIG. 12, and reference numeral HR may be a heat ejection unit for ejecting heat of the first light source unit 100 and the second light source unit 200.

Thus, when 100 at least one of the first terminal 150 provided in the rear side of the first light source unit 100 and the second terminal 250 provided in the rear side of the second light source unit 200 passes through the via hole, the size of the substrate 400 and the light emitting unit 10 may become smaller.

Meanwhile, when the first light source unit 100 emits light, the second light source unit 200 may not emit light, and, when the first light source unit 100 does not emit light, the second light source unit 200 may emit light.

That is, the first light source unit 100 may operate as a main light source of the endoscope system, and the second light source unit 200 may operate as a backup light source in the event of failure of the first light source unit 100. Accordingly, a stable operation of the endoscope system may be achieved.

The endoscopic system according to an embodiment of the present disclosure can reduce a size by reducing a distance between a first light source and a second light source.

Hereinabove, although the present disclosure has been described with reference to exemplary embodiments and the accompanying drawings, the present disclosure is not limited thereto, but may be variously modified and altered by those skilled in the art to which the present disclosure pertains without departing from the spirit and scope of the present disclosure claimed in the following claims.

What is claimed is:

1. An endoscope system comprising:
   a first light source unit configured to be provided on a substrate, and to have a first terminal to which power is supplied; a second light source unit configured to be provided on the substrate, and to have a second terminal to which power is supplied;
   an optical fiber configured to guide a light of the first light source unit and the second light source unit to a target object;
   an image sensing unit configured to sense the light reflected and reached from the target object to convert into an image signal; and
   an image signal processing unit configured to process the image signal to display on a display unit,
   wherein the first terminal and the second terminal are disposed on an area in which the first light source unit and the second light source unit do not face each other, respectively,
   wherein the first light source unit and the second light source unit are disposed in a virtual opening region which is extended from an opening of the optical fiber.

2. The endoscope system of claim 1, further comprising an optical unit configured to input light of the first light source unit and the second light source unit into the optical fiber.

3. The endoscope system of claim 1, wherein the area is a side surface of the first terminal and the second terminal or a rear side surface of the first terminal and the second terminal.

4. The endoscope system of claim 1, wherein the first light source unit and the second light source unit includes LED, respectively.

5. The endoscope system of claim 1, wherein the second light source unit does not emit light when the first light source unit emits light, and the second light source unit emits light when the first light source unit does not emit light.

* * * * *